United States Patent
Joyce et al.

(10) Patent No.: US 11,275,069 B2
(45) Date of Patent: Mar. 15, 2022

(54) DETECTION OF NON-XR/MD DETECTABLE FOREIGN OBJECTS IN MEAT

(71) Applicant: Mettler Toledo LLC, Columbus, OH (US)

(72) Inventors: Gary Joyce, Hudson, FL (US);
Richard Hebel, New Port Richey, FL (US)

(73) Assignee: METTLER-TOLEDO, LLC, Columbus, OH (US)

(*) Notice: Subject to any disclaimer, the term of this patent is extended or adjusted under 35 U.S.C. 154(b) by 216 days.

(21) Appl. No.: 16/507,505

(22) Filed: Jul. 10, 2019

(65) Prior Publication Data
US 2021/0010987 A1    Jan. 14, 2021

(51) Int. Cl.
*G01N 33/12* (2006.01)
*B07C 5/34* (2006.01)
(Continued)

(52) U.S. Cl.
CPC .......... *G01N 33/12* (2013.01); *B07C 5/3416* (2013.01); *G01N 21/85* (2013.01); *B07C 2501/0081* (2013.01); *G01N 27/82* (2013.01)

(58) Field of Classification Search
CPC ......... B07C 5/10; B07C 5/342; B07C 5/3416; B07C 5/366; G01N 33/12; G01N 21/84; G01N 21/85; G01N 27/82
(Continued)

(56) References Cited

U.S. PATENT DOCUMENTS

| 9,310,512 | B1* | 4/2016 | Kane | G01V 8/00 |
| 2003/0034282 | A1* | 2/2003 | Satai | B07C 5/366 |
| | | | | 209/582 |

(Continued)

FOREIGN PATENT DOCUMENTS

| DE | 202006010023 U1 | 12/2006 |
| EP | 0146299 A1 | 6/1985 |

(Continued)

OTHER PUBLICATIONS

International Search Report and Written Opinion of the International Searching Authority (Forms PCT/ISA/237, PCT/SA/210 and PCT/ISA/220) dated Nov. 4, 2020, by the European Patent Office in corresponding International Application No. PCT/US2020/041566. (14 pages).

*Primary Examiner* — Terrell H Matthews
(74) *Attorney, Agent, or Firm* — Buchanan Ingersoll & Rooney PC

(57) ABSTRACT

Disclosed is an inspection system having a background positioned adjacent an inspection zone; and an image capturing device configured to receive background electromagnetic radiation (EMR) from the background and from the inspection zone, the inspection zone being configured and arranged to receive material for transport into the inspection zone; wherein the background has a background property defined by a background emission, a background absorbance, and a background reflectance, the background property being matched in EMR to a material EMR of material to be transported into the inspection zone, the material having a material property defined by a material emission, a material absorbance, and a material reflectance; and wherein the image capturing device is configured to detect a foreign object within material when transported into the inspection (Continued)

zone by deducting the background EMR from the material EMR.

19 Claims, 6 Drawing Sheets

(51) Int. Cl.
    *G01N 21/85*      (2006.01)
    *G01N 27/82*      (2006.01)

(58) Field of Classification Search
    USPC .......................................................... 209/577
    See application file for complete search history.

(56) References Cited

U.S. PATENT DOCUMENTS

| | | | | |
|---|---|---|---|---|
| 2015/0336135 | A1* | 11/2015 | Corak | B07C 5/367 |
| | | | | 800/320.1 |
| 2016/0263624 | A1* | 9/2016 | Balthasar | B07C 5/3416 |
| 2018/0365822 | A1* | 12/2018 | Nipe | G06K 9/46 |
| 2018/0369870 | A1* | 12/2018 | Justice | B07C 5/3416 |

FOREIGN PATENT DOCUMENTS

| | | | | |
|---|---|---|---|---|
| EP | 3242124 | A1 | 11/2017 | |
| WO | 2017048783 | A1 | 3/2017 | |
| WO | WO-2017048783 | A1 * | 3/2017 | ............. G01N 33/02 |

* cited by examiner

DETECTION OF NON-XR/MD DETECTABLE FOREIGN OBJECTS IN MEAT

FIELD

Embodiments can relate to an inspection system having a background positioned adjacent an inspection zone, wherein an image capturing device receives electromagnetic radiation from the background and from the inspection zone to identify foreign objects traveling through the inspection zone.

BACKGROUND INFORMATION

Conventional inspection systems generally rely on x-ray (XR) or Mahalanobis Distance (MD) techniques and are able to detect a wide range of contaminants and other quality related non-conformances. Yet, there are some foreign object contaminants that cannot be detected by XR or MD techniques, resulting in a non-Mt/MD detectable event. Non-XR/MD detectable events are common for inspection systems used in meat processing systems (i.e., where the material being inspected is meat). Foreign objects leading to a non-XR/MD detectable event can include items such as cardboard, plastic materials from liners and conveyors, cutting knives and hooks, personal protective equipment such as earplugs, gloves, and hairnets, pocket items including pens, pencils, and candy wrappers, etc. Such events represent a significant cost and burden to the entities engaged in meat processing.

In addition, conventional systems cannot detect a foreign object contaminant being conveyed through the system in the absence of the meat flow (i.e., when no meat is being conveyed but the conveyor is running and is transporting a foreign object that had been inadvertently entrained in the system).

Known means to remedy these deficiencies are the use of human inspectors that visually inspect the meat before or after it is transported through the XR and/or MD detector, but prior to the meat entering the grinder. Such techniques are labor intensive and are limited in effectiveness, as human inspectors are constrained to visual inspection and can only seeing the top layer of the meat. Yet, many foreign objects are hidden within the meat or lie under the meat at the meat/conveyor interface. In addition, eye/vision fatigue experienced by human inspectors sets in after a period of time, which further reduces the effectiveness of the human inspector to identify foreign objects.

Known inspection systems can be appreciated from DE 202006010023, EP 3242124, US 20150336135, US 20160263624, and WO 2017048783. Known systems can be limited in that they cannot effectively and efficiently detect non-XR/MD detectable events. Known systems are also limited in their ability to detect foreign objects being conveyed through the processing system in the absence of meat flow.

SUMMARY

Embodiments can relate to an inspection system having a background positioned adjacent an inspection zone, an image capturing device configured to receive background electromagnetic radiation (EMR) from the background and from the inspection zone, the inspection zone being configured and arranged to receive material for transport into the inspection zone. The background has a background property defined by a background emission, a background absorbance, and a background reflectance, the background property being matched in EMR to a material EMR of material to be transported into the inspection zone, the material having a material property defined by a material emission, a material absorbance, and a material reflectance. The image capturing device is configured to detect a foreign object within material when transported into the inspection zone by deducting the background EMR from the material EMR.

Embodiments can relate to a material processing system having a conveyor system having a conveyor belt configured to carry material, the conveyor belt including an outfeed conveyor belt being positioned so that the material will fall through an inspection zone and land on the outfeed conveyor belt. The material processing system can include an inspection system having: a background positioned adjacent the inspection zone; and an image capturing device configured to receive EMR from the background and from the inspection zone, the inspection zone being configured and arranged to receive material for transport into the inspection zone. The background has a background property defined by a background emission, a background absorbance, and a background reflectance, the background property being matched in EMR to a material EMR of a material to be transported into the inspection zone, the material having a material property defined by a material emission, a material absorbance, and a material reflectance. The image capturing device is configured to detect a foreign object within material when transported into the inspection zone by deducting the background EMR from the material EMR.

Embodiments can relate to a method for inspection involving positioning a background adjacent an inspection zone, the background having a background property defined by a background emission, a background absorbance, and a background reflectance. The method can involve directing material of a material flow into the inspection zone, the material having a material property defined by a material emission, a material absorbance, and a material reflectance. The method can involve detecting whether the material property differs from the background property by at least deducting EMR of the background from EMR of the material.

BRIEF DESCRIPTION OF THE DRAWINGS

Other features and advantages of the present disclosure will become more apparent upon reading the following detailed description in conjunction with the accompanying drawings, wherein like elements are designated by like numerals, and wherein.

DETAILED DESCRIPTION

Figure 1:
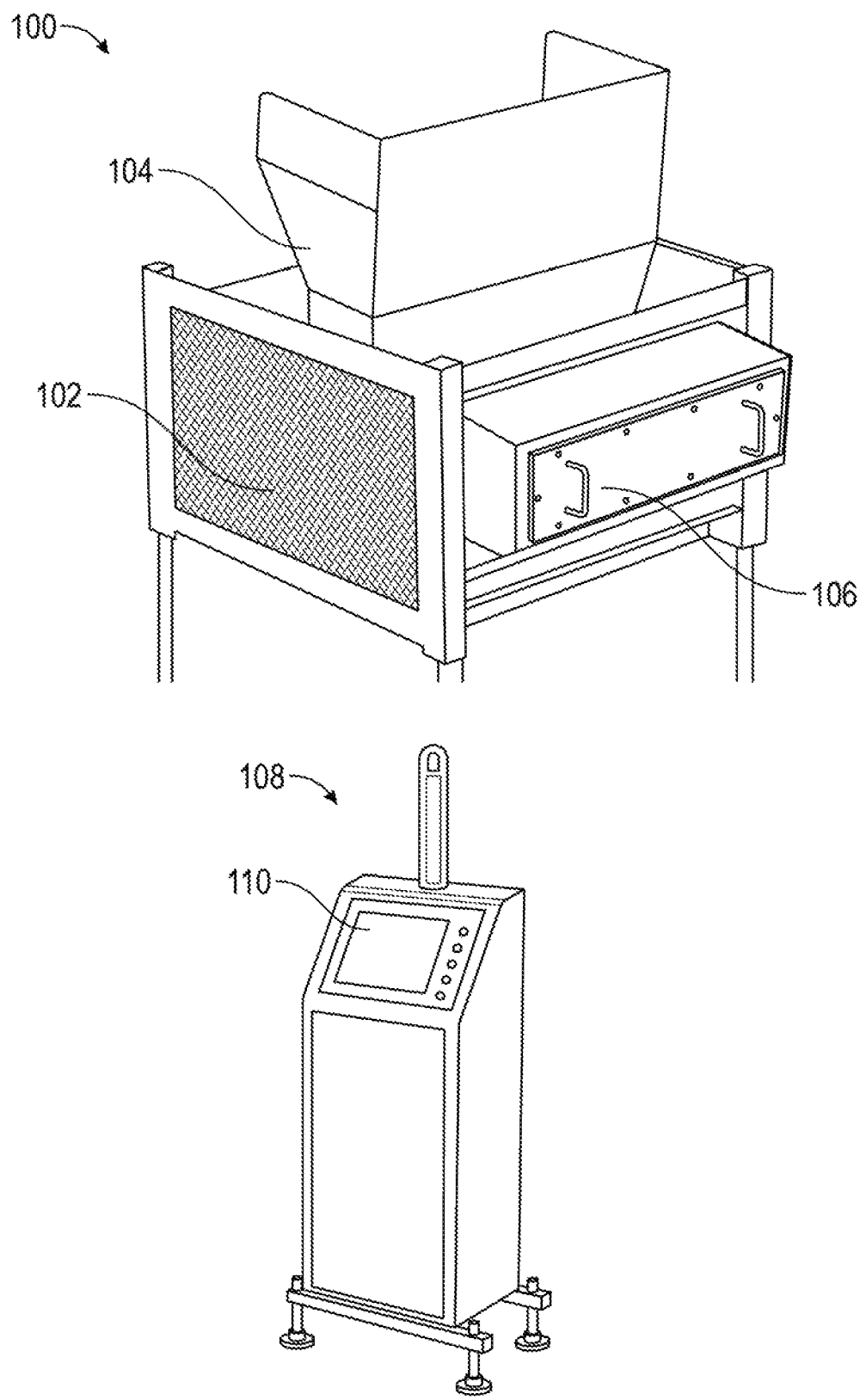
FIG. 1 shows an exemplary inspection system.
Figure 2:
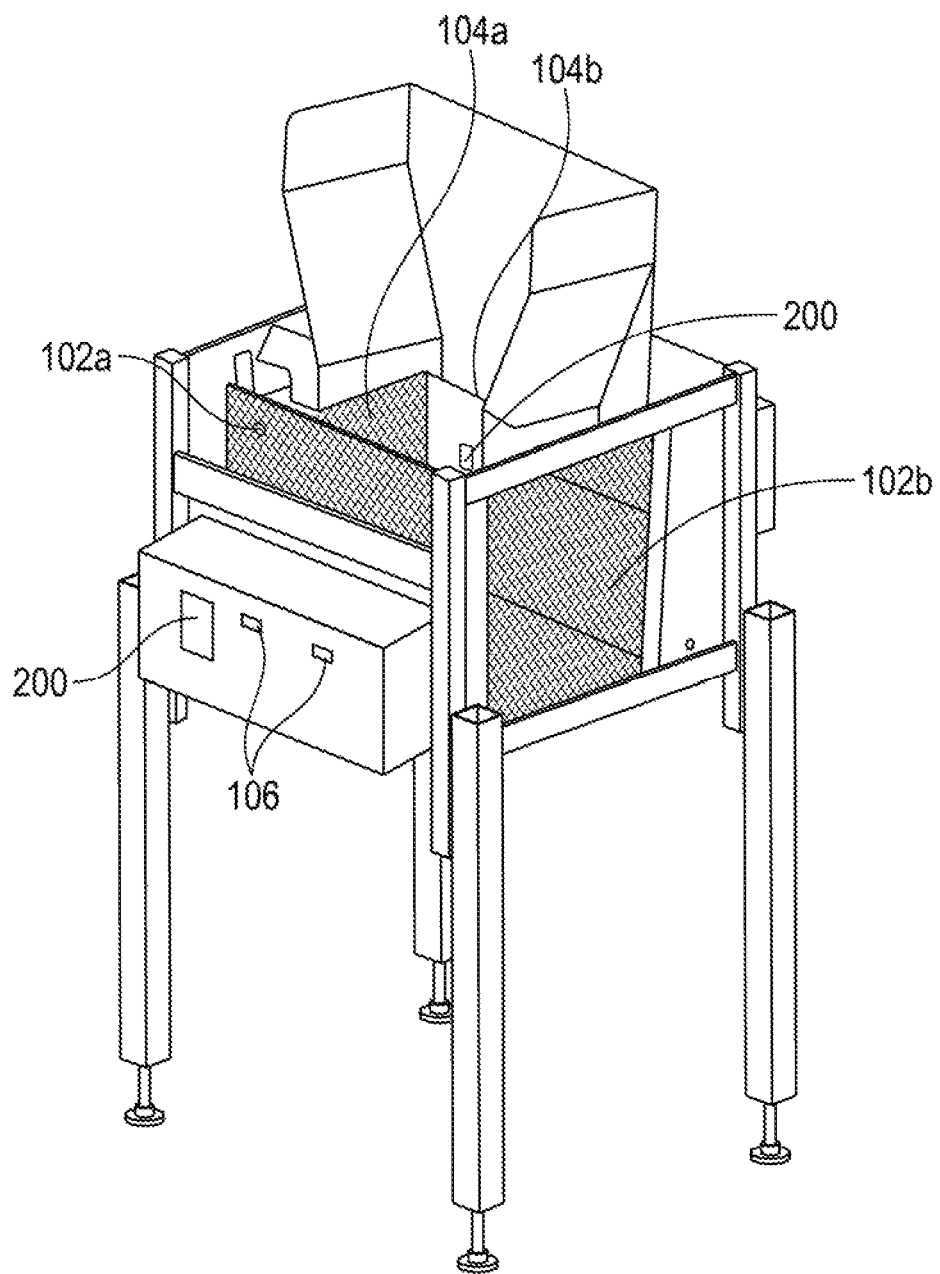
FIG. 2 show an exemplary configuration of an embodiment of the inspection system.
Figure 3:
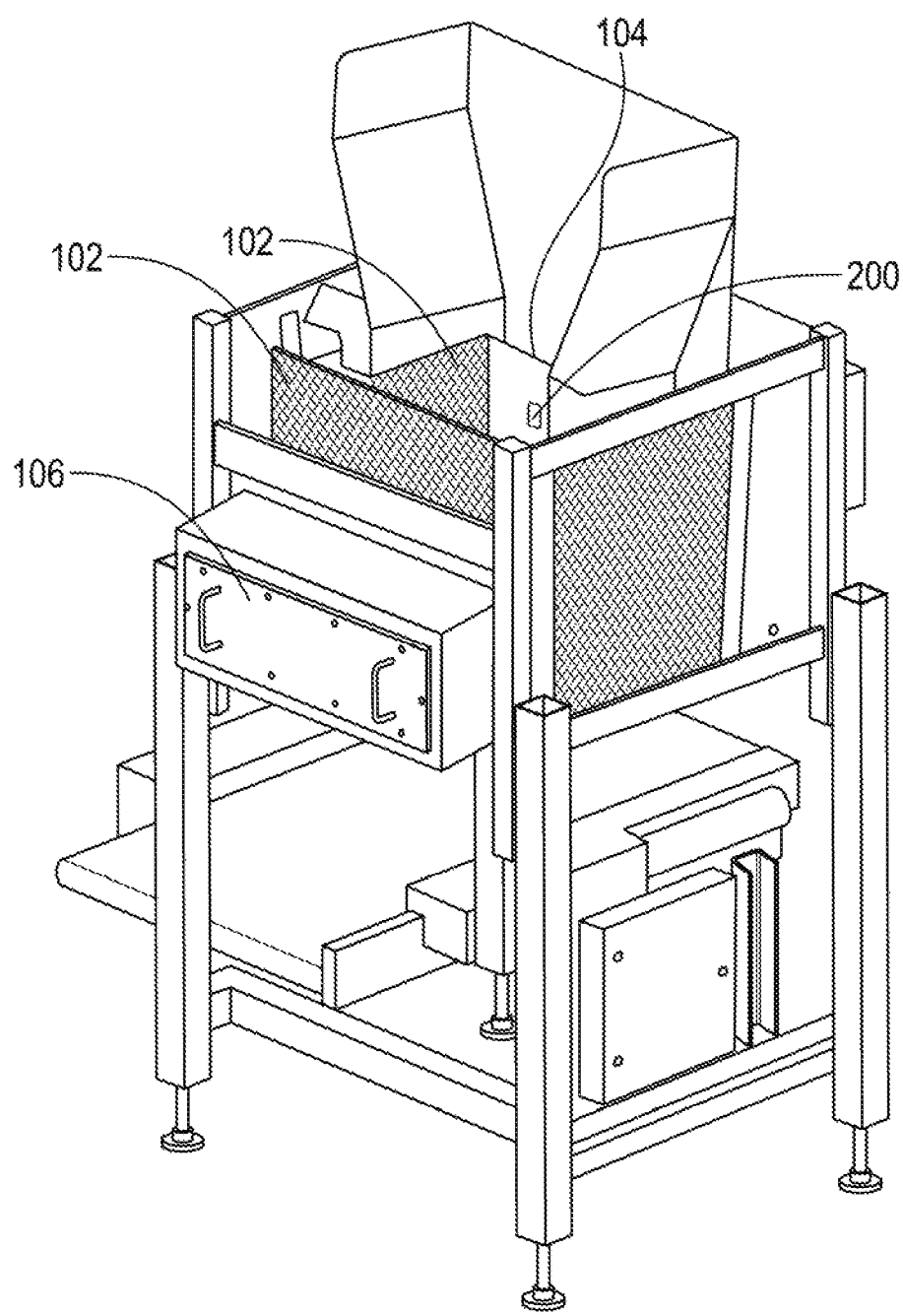
FIG. 3 shows another exemplary configuration of an embodiment of the inspection system.

Referring to FIGS. 1-3, embodiments can relate to an inspection system 100 having a background 102 positioned adjacent an inspection zone 104, and an image capturing device 106 configured to receive background electromagnetic radiation (EMR) from the background and from the inspection zone 104, the inspection zone 104 being configured and arranged to receive material for transport into the inspection zone 104.

The inspection system 100 can be an apparatus designated for inspecting material entering into and/or passing through an inspection zone 104 to determine if the material is a foreign object and/or determine if the material has a foreign object entrained therein (e.g., a foreign object mixed in it, on top of it, underneath it, etc.). For instance, the inspection system 100 may be part of a material processing system 500 (e.g., a meat processing system). The material processing system 500 can have a conveyance system that causes the material to pass through the inspection zone 104. The inspection zone 104 can be a designated area of the material processing system 500 used to inspect the material for quality assurance purposes. It is contemplated for the inspection zone 104 to be an area of the conveyance system through which the material falls through in a free-fall. For example, the conveyance system can include a conveyor belt 502 having an infeed conveyor belt 502a and an outfeed conveyor belt 502b, the infeed conveyor belt 502a being positioned relative to the outfeed conveyor belt 502b so that the material will fall from the infeed conveyor belt 502a, travel through an inspection zone 104, and land on the outfeed conveyor belt 502b. The portion of the conveyance system where the material falls from the infeed conveyor belt 502a to the outfeed conveyor belt 502b can be referred to as a waterfall region 504. Having the inspection zone 104 configured as a designated area for inspection of material entering a free-fall can be beneficial in that the inspection system 100 can better be able to detect foreign objects that would otherwise lie underneath the layer of meat while on the conveyor belt 502.

The inspection system 100 can be used to identify whether any material passing through the inspection zone 104 is a substance other than meat. Thus, the inspection system 100 can identify an object (whether it is within the meat, separate from the meat, passing through the inspection zone 104 simultaneously with the meat, passing through the inspection zone 104 in the absence of meat, etc.) passing through the inspection zone 104 as a substance other than meat. For instance, the inspection system 100 can determine if the meat flow passing through the inspection zone 104 has been contaminated with a foreign object (e.g., a piece of equipment from the material processing system 500 has worked loose and is being transported by the conveyance system along with the meat) and/or determine if a foreign object passes through the inspection zone 104 even if no meat is being transported through the inspection zone 104 (e.g., a worker has lost a glove and it is being transported by the conveyance system in the absence of meat being flowed through the system). The foreign object can be any substance not anticipated to be part of the meat or meat mix, such as cardboard, plastic materials from liners and conveyors, cutting knives and hooks, personal protective equipment such as earplugs, gloves, and hairnets to pocket items including pens, pencils, candy wrappers, etc.

The inspection system 100 can have a background 102 positioned adjacent the inspection zone 104. The inspection zone 104 can be a volume of space designated for conducting inspection of material entering into the inspection zone 104. The background 102 can be an object (e.g., a sheet, a backboard, etc.) placed adjacent (e.g., in proximity to, abutting against, etc.) this volume of space so that at least a portion of the background 102 is within a field of view (the angular extent of a given scene) of the volume of space. As will be explained herein, being within the field of view will allow EMR from an illumination source 200 to be directed to both the inspection zone 104 and the background 102, and allow EMR emitted from both material within the inspection zone 104 and the background 102 to be received by the image capturing device 106.

The background 102 can be configured to have a background property defined by a background emission, a background absorbance, and a background reflectance, the background property being matched in EMR to a material EMR of material to be transported into the inspection zone 104, the material having a material property defined by a material emission, a material absorbance, and a material reflectance. For instance, the background property can be configured to have optical properties that match those of the material (e.g., meat), but not that of any anticipated foreign objects. It is possible for a foreign object (e.g., a non-anticipated foreign object) to have optical properties that match those of the background property, but the chances of this eventuality occurring is expected to be low. For instance, if the material is meat and the meat is being processed by a meat processing system, it can be determined with a high level of statistical certainty what the optical properties of the meat will be (because the composition of the meat mix will be known due to the meat is being processed under controlled conditions) and what the optical properties of the foreign objects will be due to the limited number of possible foreign objects that can exist under such controlled conditions. Thus, the material property of meat can have a signature material emission, a signature material absorbance, and a signature material reflectance, and the background can have a background emission, a background absorbance, and a background reflectance that matches, or at least substantially matches the meat's signature material emission, a signature material absorbance, and signature material reflectance so that the background property, when detected by optical equipment, appears the same as the meat property. In other words, the optical equipment may not detect a difference in EMR emitted therefrom when comparing the background property to the material property. However, because the anticipated foreign object is expected to have a foreign object property (e.g., a foreign object emission, a foreign object absorbance, and a foreign object reflectance) that differs from those of the meat and the background, the optical equipment will detect a difference in EMR emitted therefrom when comparing the background property to the foreign object property.

While it is contemplated for the inspection system 100 to operate by detecting and comparing optical properties, such as emission, absorbance, and reflectance, other optical properties (e.g., refraction, polarization, photoluminescence, transmittance, diffraction, dispersion, dichroism, scattering, birefringence, photosensitivity, etc.) can be used in addition to or in the alternative of emission, absorbance, and reflectance.

The image capturing device 106 can be configured to detect a foreign object within material when transported into the inspection zone 104 by deducting the background EMR from the material EMR. The image capturing device 106 can be positioned so that the inspection zone 104 and at least a portion of the background 102 are within the field of view of the image capturing device 106. The image capturing device 106 can be an optical apparatus configured to receive EMR and analyze the EMR based on the wavelength, amplitude, phase, polarization, etc. For instance, the image capturing device can include a lens, a charged coupled device (CCD), and circuitry (e.g., processor, filter circuits, etc.) to receive EMR, process it, and generate an output that is the EMR comparison (the deduction of the background EMR from the material EMR). Use of the lens and the CCD for the image capturing device are exemplary, and it should be understood that optical elements and sensors in addition to or in the alternative of the lens and the CCD can be used.

The circuitry of the image capturing device 106 can be configured to compare the background property to the material property by comparing the background EMR it receives from the background 102 to the material EMR it receives from material entering into the inspection zone 104. One way to achieve this is to deduct the background EMR from the received EMR. For instance, the image capturing device 106 can receive EMR from the inspection zone 104 (whether there is material or foreign objects passing through or not) and receive EMR from the background 102. The image capturing device 106 can perform signal processing operations (e.g. Fourier transform or other operation) to allow for mathematical representation and manipulation of the received EMR. The image capturing device 106 then deducts the background EMR from the received EMR (e.g., subtracts values representative of amplitude, frequency, phase, etc. of the background EMR from values representative of amplitude, frequency, phase, etc. of the received EMR). When no material or foreign object is passing through the inspection zone 104, the image capturing device will only receive the background EMR as the received EMR, wherein deducting the background EMR from the received EMR in this case will result in background EMR, which can be defined as a negative reading (meaning no foreign object detected). When only material that is meat is passing through the inspection zone 104, the image capturing device will receive the background EMR and the material EMR as the received EMR, wherein deducting the background EMR from the received EMR in this case will result in a null reading because the background EMR and the material EMR are matched, which again can be defined as a negative reading. When only material that is a foreign object is passing through the inspection zone 104, the image capturing device will receive the background EMR and the foreign object EMR as the received EMR, wherein deducting the background EMR from the received EMR in this case will result in an EMR difference because the background EMR and the foreign object EMR are not matched, which can be defined as a positive reading (meaning that a foreign object has been detected). When material that is meat and a foreign object is passing through the inspection zone 104, the image capturing device will receive the background EMR, the material EMR, and the foreign object EMR as the received EMR, wherein deducting the background EMR from the received EMR in this case will again result in a positive reading because the background EMR and the foreign object EMR are not matched.

As noted herein, the background property can be configured to match or substantially match that of the material property (e.g., the meat). As there will be some variance in the material property (due to the different types of meat and meat mixes being processed), a threshold range can be set when performing the EMR comparison. For instance, if the EMR comparison results in a difference in EMR when the deduction is made, but that difference is within a predetermined threshold range then it still may be considered a negative reading.

As can be appreciated from the above analyses, making such a comparison (deducting the background EMR from the received EMR) facilitates detecting a foreign object passing into the inspection zone 104 regardless of whether meat is also passing into the inspection zone 104. It should also be noted that the image capturing device 106 can make the comparison by deducting the background EMR from the received EMR or by deducting the received EMR from the background EMR.

In some embodiments, the inspection system 100 can include the material positioned in the inspection zone 104. In some embodiments, the inspection system 100 can include the foreign object within the material positioned in the inspection zone 104. As noted herein, some embodiments of the inspection system 100 can be configured to inspect the material that is meat.

Some embodiments of the inspection system 100 can include a computer device 108 in operative communication with the image capturing device 106, the computer device 108 having a display 110 for displaying an image or graphical representation of the material property and the background property. The computer device 108 can be a processor in operative association with a memory. The memory can include computer program code stored thereon.

Any of the processors disclosed herein can be at least a one of a scalable processor, a parallelizable processor, etc. Any of the processors can be optimized for multi-thread processing capabilities. In some embodiments, the processor can be a graphics processing unit (GPU). The processor can include any integrated circuit or other electronic device (or collection of devices) capable of performing an operation on at least one instruction, which can be any one or combination of a Reduced Instruction Set Core (RISC) processor, a CISC microprocessor, a Microcontroller Unit (MCU), a CISC-based Central Processing Unit (CPU), a Digital Signal Processor (DSP), etc. The hardware of such devices may be integrated onto a single substrate (e.g., silicon "die"), or distributed among two or more substrates. Various functional aspects of the processor may be implemented solely as software or firmware associated with the processor.

The memory can be optionally associated with the processor. Embodiments of the memory can include a volatile memory store (such as RAM), non-volatile memory store (such as ROM, flash memory, etc.) or some combination of the two. For instance, the memory can include, but is not limited to, RAM, ROM, EEPROM, flash memory, CDROM, digital versatile disk (DVD) or other optical storage, magnetic cassette, magnetic tape, magnetic disk storage or other magnetic storage device, or any other medium which can be used to store the desired information and that can accessed by the processor. The memory can be a non-transitory computer-readable medium. The term "computer-readable medium" (or "machine-readable medium") as used herein is an extensible term that refers to any medium or any memory that participates in providing instructions to the processor for execution, or any mechanism for storing or transmitting information in a form readable by a machine (e.g., a computer). Such a medium may store computer-executable instructions to be executed by a processing element, control logic, and/or data which are manipulated by a processing element and/or control logic, the medium being able to take many forms, including but not limited to, non-volatile medium, volatile medium, and transmission media.

Transmission media can include coaxial cables, copper wire and fiber optics, which can include the wires that include or form a bus. Transmission media can also take the form of acoustic or light waves, such as those generated during radio-wave and infrared data communications, or other form of propagated signals (e.g., carrier waves, infrared signals, digital signals, etc.). Forms of computer-readable media include, for example, a floppy disk, a flexible disk, hard disk, magnetic tape, or any other magnetic medium, a CD-ROM, any other optical medium, punchcards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Instructions for implementation of any of the methods disclosed herein can be stored on the memory in the form of computer program code. The computer program code can include program logic, control logic, or other algorithms that may or may not be based on artificial intelligence (e.g., machine learning techniques, artificial neural network techniques, etc.). The memory and the computer program code can be configured to cause the processor associated therewith to implement any of the methods disclosed herein.

The computer device 108 can have a display 110 configured to display an image or graphical representation of the background property, the material property, and/or the foreign object property. For instance, the image capturing device 106 can generate an output signal that is representative of the EMR comparison (e.g., the deduction of the background EMR from the received EMR) for a point within a grid, the grid being a virtual geometric plane passing through a longitudinal axis of the inspection zone 104. The point on the grid can be a coordinate point (e.g., a Cartesian coordinates) of the grid so that a plurality of output signals can represent an EMR comparison from a plurality of points on the grid. The computer device 108 can receive these signals and generate an image or graphical representation of the EMR comparison at a point in time for the plurality of output signals. The inspection system 100 can be configured to transmit the output signals from the image capturing device 106 to the computer device 108 (and the computer device 108 can generate a display of the same) on a continuous basis, periodic basis, as dictated by a user of the inspection system 100, or by some other scheme. The computer device 108 can transmit the image or graphical representation to the display 110. The display 110 can display the image or graphical representation by causing a pixel to generate a predetermined color for a negative reading and another predetermined color for a positive reading. A user viewing the display 110 can ascertain that a foreign object has passed into the inspection zone 104 by viewing the different colors of the pixels on the display. In some embodiments, the computer device 108 can be equipped with a clock, and assign a timestamp to each output signal received by the image capturing device 106. The image or graphical representation can then be displayed on the display 110 along with the timestamp, allowing a user to determine when a foreign object has passed into the inspection zone 104.

In some embodiments, the background property is selected as a function of a material which includes a first material and a foreign object material, wherein the first material has a first material property and the foreign object material has a second material property. The first material property equals the background property, and the second material property does not equal the background property. As noted herein, the background property can be configured to have optical properties that match those of the material (e.g., meat or the first material) but not that of any anticipated foreign objects. For instance, the first material property can have a first material signature material emission, a first material signature material absorbance, and a first material signature material reflectance, and thus the background can have a background emission, a background absorbance, and a background reflectance that matches, or at least substantially matches the first material's signature material emission, signature material absorbance, and signature material reflectance so that the background property, when detected by optical equipment, appears the same as the first material (or meat) property. The anticipated foreign object is expected to have a second material property (e.g., a second material emission, a second material absorbance, and a second material reflectance) that differs from those of the first material and the background, and thus the optical equipment will detect a difference when comparing the background property to the second material property.

As noted herein, embodiments of the processors for the image capturing device 106 and/or the computer device 108 can have computer program code stored thereon that is based on artificial intelligence. The artificial intelligence can be configured to provide machine learning for the inspection system 100 so as to optimize detection. In an exemplary embodiment, the artificial intelligence can be configured to use adversarial learning techniques during image processing for detection optimization.

Conventional image processing methods use a multivariate statistical technique for detecting outliers (e.g., the Mahalanobis Distance (MD)), which utilize a single feature vector: color. This is calculated from a 3-dimensional RGB (color) input space, where the distance in the transformed space from each target pixel to the trained or "learned" distribution of "meat colors" determines whether that pixel is a "meat" or "not meat" color. In this technique, color is the sole feature vector providing discrimination between "meat" and "not meat". In effect, MD is providing anomaly detection, where the presence of a "not meat" color region in an image is an anomaly. These anomalies are then classified as foreign objects.

One of the problems with conventional MD methods is that certain classes of foreign objects may be very similar to "meat color", or may be translucent/transparent where they do not exhibit a color but appear to be the same color as whatever object may be in their background. Further, how the foreign objects are presented in the meat matrix (where they are presented as a result of reflected and transmitted light from primary illumination sources and secondary reflection from the illumination source in the inspection zone) can confound color discrimination. This limits how well the system "learns" during supervised learning, but also limits discrimination performance at run-time, which can increase false reject rate.

In addition, some foreign object classes that consist of man-made (manufactured) product, regardless of color, exhibit signature spatial features discriminable from natural product like meat, like straight edges (or more generally, edge characteristics), precisely repeatable forms (example: texture in fabric), or fine/dispersed distribution disjoint forms (example: fiber in cardboard), precise parallels, concentricities, regular geometric forms (example: tape, washers, coins, o-rings), etc., which can render anomaly detection via MD difficult. For instance, practically, it cannot be known a priori how (and to what extent) the discriminant hyperplane in that space will be determined by the feature vectors (and combinations thereof). Furthermore, it is not practical to use a technique that requires an exhaustive training set due to the universe of foreign object classes/specimens being boundless. Thus, there is a large set (actually open-ended set) of "spatial" feature vectors that the conventional algorithmic methods are naïve/blind to. Combined with color feature vector(s), this set of spatial feature vectors poses a very high dimension data space.

Embodiments of the adversarial learning technique, however, utilize a convolutional neural network (CNN), which can be used as part of Generative Adversarial Network or "GAN". CNNs and GANs are based on deep learning techniques that center on effective methods in high dimension data spaces. More particularly, the GAN can be configured so that two networks compete "adversarially" with each other during training: one network ("generator") generates real negative images and fake negative images (negative meaning no foreign objects) from random noise; the other network ("discriminator")—which has access to the training images—attempts to discern (classify) which of the images from the generator are real and which are fake. These two networks can be placed into a feedback loop with each other, in which the generator "learns" by becoming more proficient at generating fake images that can fool the discriminator, while the discriminator "learns" by becoming more proficient at not being fooled (i.e., better at discerning the difference between real and fake images). This technique for anomaly detection can provide a significant advance in any imaging-based inspection application (optical, IR, x-ray, etc.).

Embodiments of the adversarial learning technique can provide the following advantages Training set. Typically, it is difficult and expensive to create large populations of images with foreign object samples required by conventional methods. Embodiments of the adversarial learning technique, however, can use a large population of negative images (i.e., no foreign objects), which are easily and essentially cost-fee to acquire.

Unsupervised Learning. Conventional methods require "supervised learning", meaning the system is trained using samples that are labeled (i.e., it is known a priori what class each sample belongs to). Embodiments of the adversarial learning technique, however, can utilize unsupervised learning, where it is left to the algorithm to develop and discern these distinctions.

Generalization. A characteristic advantage neural network algorithms in classification schemes is their ability to "generalize": They do not need to have exhaustive training to address every possible input state. When presented with novel input, they will tend to classify accurately, at least within the dimensions of their feature vector space. In vision applications, that translates into a substantially enhanced ability to discern subtle and perhaps incomplete patterns in a noisy image, without the tendency to fail catastrophically (something that simple thresholding and pixel counting often do).

Extensibility. Embodiments of the adversarial learning technique can be extended to incorporate additional feature vectors from other imaging modalities, including NIR and XR, for example.

Limitation of Mahalanobis Distance. MD can work well, but only when the underlying data sets are normal and unimodal. Embodiments of the adversarial learning technique are not reliant on normal and unimodal data sets. In addition, MD is less than effective with chroma discrimination within low saturation colors, which tend to predominate in imaging for meat processing.

Embodiments of the adversarial learning technique do not rely on a human (qualified or not) to determine appropriate training or discriminant functionality. Instead, the system can develop these itself from adversarial training.

In some embodiments, the inspection system 100 can include an illumination source 200 configured to generate and direct EMR into the inspection zone 104 so that the EMR will interact with the background 102 and will interact with the material when the material travels into the inspection zone 104. The illumination source 200 can be an incandescent lamp, halogen lamp, a light emitting diode, a laser, an IR light generator, a UV light generator, an x-ray generator, etc. It is contemplated for the illumination source 200 to be a stroboscopic lamp so as to provide the requisite EMR intensity for effective and efficient operation of the inspection system 100. For instance, the intensity of the EMR required to analyze meat being conveyed in a material processing system 500 would be high, thus a stroboscopic lamp (e.g., in continuous mode for example) would be able to generate the requisite intensity in an efficient manner.

In some embodiments, illumination source 200 can be configured to generate EMR having a wavelength in the visible spectrum. While the illumination source 200 can be configured to generate EMR at any wavelength in the EMR spectrum, it is contemplated for the illumination source to generate EMR in the visible spectrum (e.g., wavelengths within the range from 400 nm to 700 nm). It is further contemplated for the illumination source to generate white light (light comprising all, or substantially all, of the wavelengths in the visible spectrum, each with equal, or substantially equal, intensity).

The image capturing device 106 can be an optical camera (e.g., RGB camera, HLS camera, etc.). With embodiments of the inspection system 100 configured to analyze EMR of the visible spectrum, the image capturing device 106 can be an optical camera. However, if in addition or in the alternative, the EMR analysis includes an analysis of EMR outside of the visible spectrum, the image capturing device 106 can be or include other components for such analysis (e.g., an antenna, a telescope, a spectroscope, an IR detector or camera, a NIR detector or camera, a UV detector or camera, X-ray detector, etc.)

In an exemplary embodiment, the material can include a first material and a foreign object material, wherein the first material has a first material property and the foreign object material has a second material property. The first material property can cause the EMR interacted therewith to be within the red color spectrum and the background property can cause the EMR interacted therewith to be within the red color spectrum. As noted herein, the material can be meat, such as bulk flow of trim meat (e.g., beef, pork, lamb, turkey, chicken, etc.). Such meat (uncooked and unprocessed) generally has a red color (e.g., EMR emitted therefrom has wavelengths generally within the range from 625 nm to 675 nm). Thus, with embodiments where the first material is meat, the background 102 can be configured to have a background property such that the EMR emitted therefrom is a red color so as to match with the EMR emitted from the first material or the meat.

In some embodiments, the inspection zone 104 can be segmented by a longitudinal plane into a first inspection zone side 104a and a second inspection zone side 104b. For instance, the inspection zone 104 can be bi-sected in the vertical direction by a longitudinal plane, forming a first inspection zone side 104a and a second inspection zone side 104b. In some embodiments, the background 102 can include a first background 102a located in the first inspection zone side 104a and a second background 102b located in the second inspection zone side 104b. Any one or combination of the first background 102a and the second background 102b can be arranged to be parallel or at any other angle with respect to the longitudinal plane.

The material can travel into the inspection zone 104 between the first background 102a and the second background 102b. The illumination source 200 can be configured to direct the EMR into the inspection zone 104 so that the EMR will interact with the first background 102a, the second background 102b, and the material when the material travels into the inspection zone 104. For instance, the illumination source 200 can be positioned so that the EMR emitted therefrom is incident upon the inspection zone 104 (and any material or foreign object passing into the inspection zone 104), the first background 102a, and the second background 102b. Some embodiments can include a plurality of illumination sources 200. For instance, a first illumination source 200 can be configured to emit EMR to be incident upon the inspection zone 104 (and any material or foreign object passing into the inspection zone 104) and the first background 102a. A second illumination source 200 can be configured to emit EMR to be incident upon the inspection zone 104 (and any material or foreign object passing into the inspection zone 104) and the second background 102b.

In some embodiments, the image capturing device 106 can include a first image capturing device 106 and a second image capturing device 106. The first image capturing device 106 can be configured to detect whether the material property differs from the background property of the first background 102a. The second image capturing device 106 can be configured to detect whether the material property differs from the background property of the second background 102b. For instance, the first image capturing device 106 can be configured to perform the EMR comparison with background EMR from the first background 102a, and the second image capturing device 106 can be configured to perform the EMR comparison with background EMR from the second background 102b.

Figure 4:
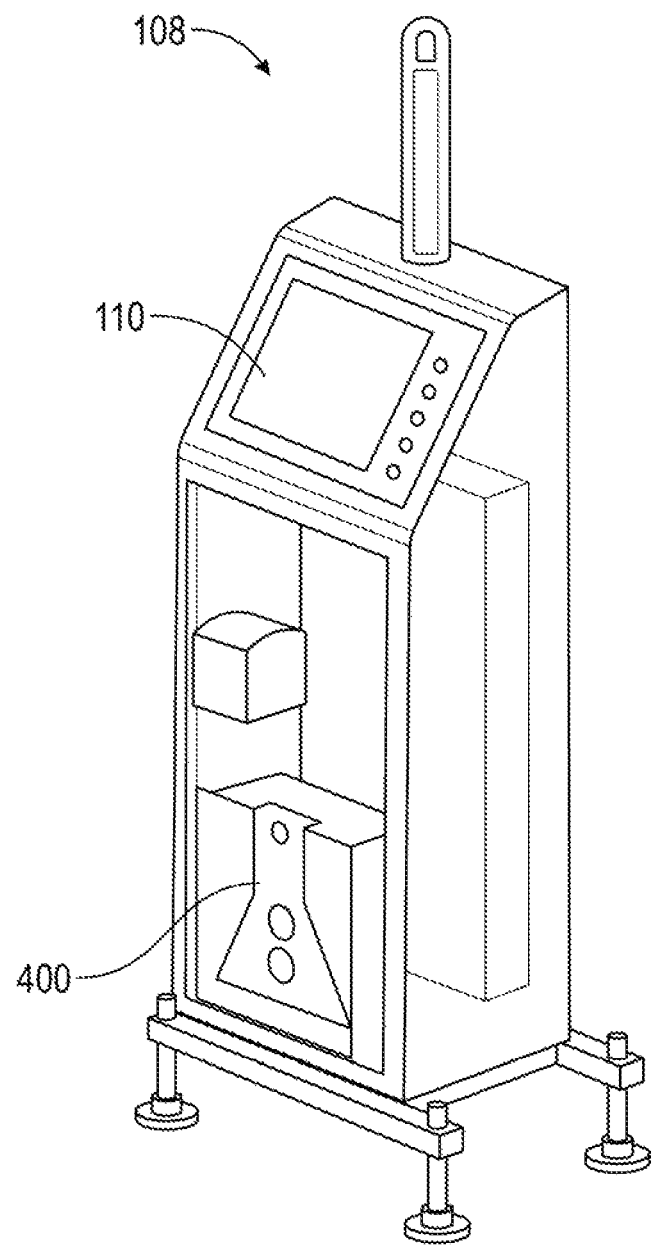
FIG. 4 shows an exemplary configuration of an embodiment of a computer device that can be used with an embodiment of the inspection system.
Figure 5:
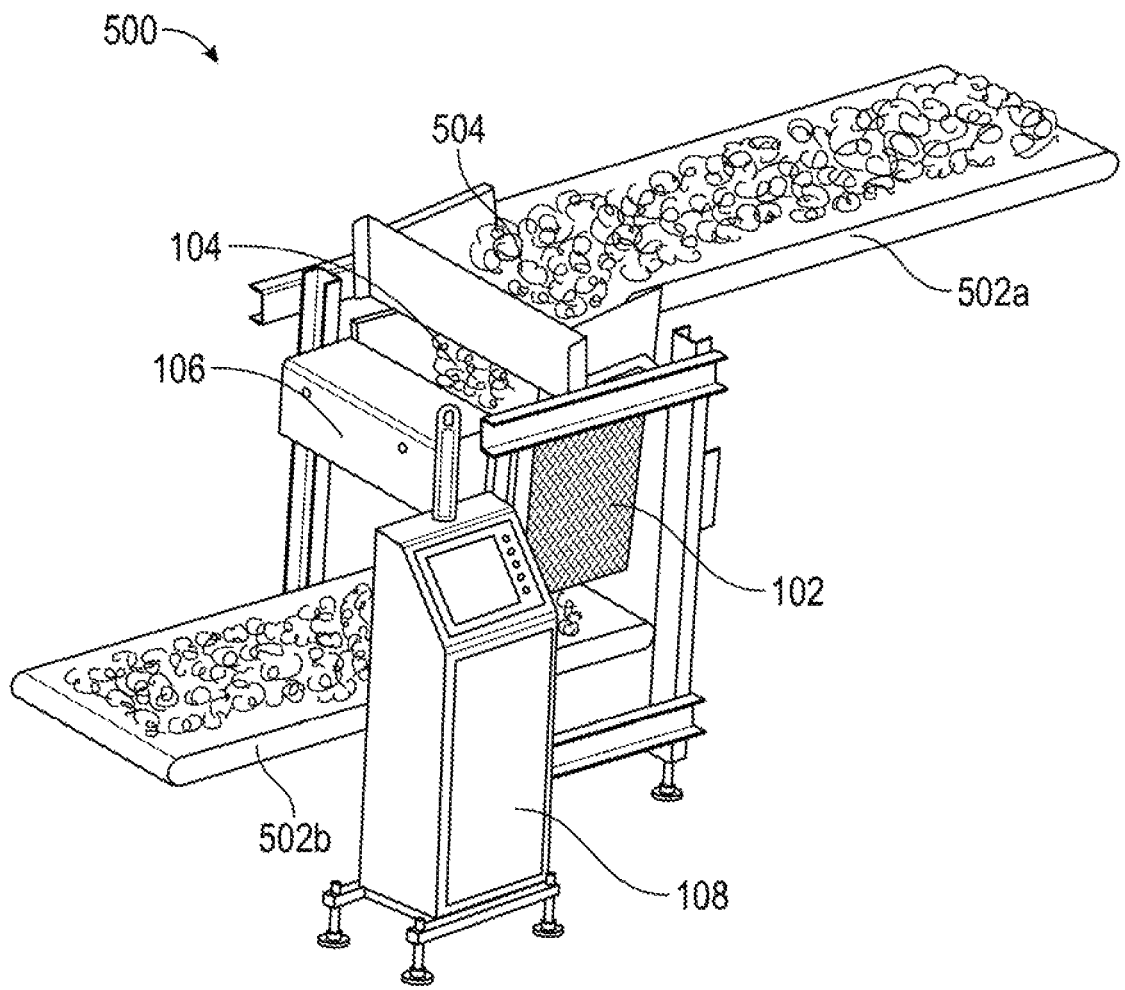
FIG. 5 shows an exemplary material processing system that can be used with an embodiment of the inspection system.

Referring to FIGS. 4-5, embodiments can relate to a material processing system 500 including a conveyance system having a conveyor belt 502 configured to carry material. The conveyor belt 502 can include an outfeed conveyor belt 502b being positioned so that the material will fall through an inspection zone 104 and land on the outfeed conveyor belt 502b. In some embodiments, the conveyor belt 502 can include an infeed conveyor belt 502a and an outfeed conveyor belt 502b. The infeed conveyor belt 502a can be positioned relative to the outfeed conveyor belt 502b so that the material will fall from the infeed conveyor belt 502a, travel through an inspection zone 104, and land on the outfeed conveyor belt 502b. The portion of the conveyance system where the material falls from the infeed conveyor belt 502a to the outfeed conveyor belt 502b can be referred to as a waterfall region 504. It will be appreciated that the conveyance system can be configured to transport material via a continuous flow process or via a discrete or batch flow process.

The material processing system 500 can include an inspection system 100 having a background 102 positioned adjacent the inspection zone 104, and an image capturing device 106 configured to receive EMR from the background 102 and from the inspection zone 104, the inspection zone 104 being configured and arranged to receive material for transport into the inspection zone 104. For instance, an embodiment of the inspection system 100 can be incorporated with or used with a material processing system 500.

Embodiments of the inspection system 100 used in or with the material processing system 500 can be configured so that the background 102 has a background property defined by a background emission, a background absorbance, and a background reflectance, the background property being matched in EMR to a material EMR of a material to be transported into the inspection zone 104, the material having a material property defined by a material emission, a material absorbance, and a material reflectance.

The image capturing device 106 can be configured to detect a foreign object within material when transported into the inspection zone 104 by deducting the background EMR from the material EMR.

In some embodiments, the material is meat and the foreign object is a contaminant.

In some embodiments, the material processing system 500 can include a computer device 108 in operative communication with the image capturing device 106, the computer device 108 having a display 110 for displaying an image or graphical representation of the background property and the material property.

The computer device 108 can include a control module 400 to control the operation of the conveyor belt 502. The control module 400 can be a processor or other circuitry and mechanics configured to control operational aspects of the conveyance system, such as activation/deactivation of the conveyor belt 502 (e.g., the infeed conveyor belt 502a, the outfeed conveyor belt 502b, or any combination of both), speed of the conveyor belt 502, directional flow of the material in the conveyance system, etc. As noted herein, it is contemplated for the inspection system 100 to be used to inspect meat. In this regard, the inspection system 100 can be used to identify any foreign object that has entered the conveyance system before the meat is further processed by the material processing system 500. Thus, the inspection system 100 can be configured so that the inspection zone 104 is positioned at a point in the conveyance system before the meat is processed (e.g. grinded). Upon detecting that a foreign object has entered into the inspection zone 104, the computer device 108 can transmit a signal to the control module 400 to cause the control module 400 to stop the conveyor belt 502, divert the material that is suspected to have the foreign object to a rejection bin, divert the material that is suspected to have the foreign object to a further inspection process, etc. The computer device 108 can transmit the signal automatically. In addition or in the alternative, a user of the computer device 108 can cause the transmission of the signal after the computer device 108 indicated that the foreign object has been detected (e.g., the computer device 108 displayed the image or graphical representation of the foreign object on the display 110). For instance, the computer device 108 can also generate a user interface via the display 110 that allows a user to issue commands and control aspects of the inspection system 100 and/or material processing system 500.

For instance, in an exemplary embodiment, meat (after passing the inspection zone 104—which can be the waterfall region 504) will land on the outfeed conveyor belt 502b for further conveyance and processing. One of the following actions can occur if a "Not Meat" condition is identified (or a foreign object is identified): a) Meat will land on the outfeed conveyor belt 502b and the computer device 108 sends a reject signal to cause the outfeed conveyor belt 502b and/or the infeed conveyor belt 502a to stop, wherein a human operator will sort through the meat to find the foreign object. Once the foreign object has been removed, the human operator can restart the conveyance system via the computer device 108 and/or the control module 400, allowing the meat to proceed to the next stage of the process, or the human operator can remove the meat (along with the suspected foreign object) and re-insert it in to the material flow path for inspection by a same or different inspection technique (e.g., MD, NIR, XR, human inspection, etc.). b) Meat will land on an outfeed conveyor belt 502b equipped with an automated reject mechanism, wherein the foreign object detection signal will cause the control module 400 to actuate the automatic rejection mechanism so as to divert the material (and the suspected foreign object) to a rejection bind for disposal or for additional sorting by a human operator. If sent for additional sorting, once the foreign object has been removed, the previously rejected material can be re-inserted to the material flow path (e.g., in a portion of the path that is before the inspection zone 104 so as to allow for the material to be inspected again) or into a material flow path for inspection by another method. c) Meat (the portion suspected to have the foreign object) will be diverted to a reverse-retracting outfeed conveyor belt 502b, while meat (not suspected of having the foreign object) will be directed to an outfeed conveyor belt 502b for further processing (e.g., grinding). The meat that lands on the reverse-retracting outfeed conveyor belt 502b will be direct to a rejection bind for disposal or for additional sorting by a human operator. If sent for additional sorting, once the foreign object has been removed, the previously rejected material can be re-inserted to the material flow path (e.g., in a portion of the path that is before the inspection zone 104 so as to allow for the material to be inspected again) or into a material flow path for inspection by another method.

In some embodiments, the user interface, along with the display of the image or graphical representation of the material and foreign object, can assist with identification and removal of the foreign object from the rejected material. For instance, the display 110 can display images of the suspected foreign object that caused the rejection to occur so as to allow the operator to see exactly what they are searching for in the material in order to speed up the process and deliver positive confirmation of the foreign object being sought.

In some embodiments, the outfeed conveyor belt 502b can be configured as a rejection path to direct the material to a rejection bin as a default unless the inspection system 100 detects a negative reading. Upon detecting a negative reading, the outfeed conveyor belt 502b can re-direct the meat to an accepting bin or acceptance path. In other words, the material processing system 500 can be configured to automatically direct the meat towards a rejection bin as a fail-safe until it is confirmed that a batch of meat contains no foreign objects (e.g., no positive readings were detected), at which time the outfeed conveyor belt 502b re-directs that batch of meat to an acceptance bin or acceptance path.

Figure 6:
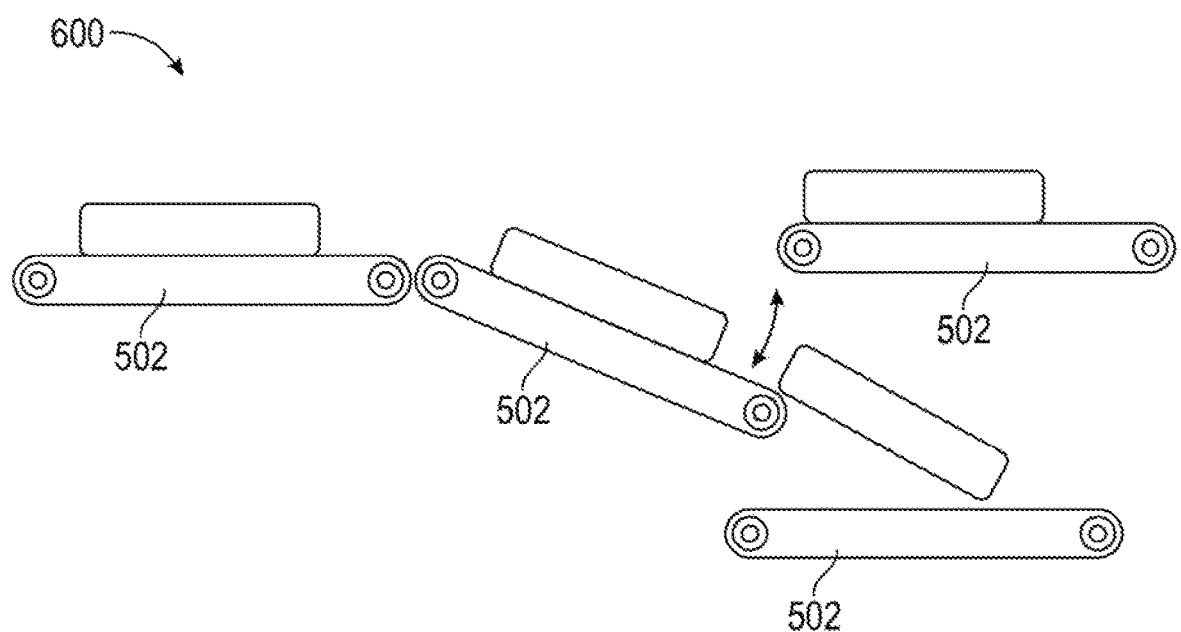
FIG. 6 shows an exemplary separator unit that may be used with an embodiment of the material processing system.

Referring to FIG. 6, in some embodiments, the material processing system 500 a separator unit 600 configured to separate and remove the foreign object from the conveyor belt 502. A separator until 600 can be a mechanical switch (e.g., a flap sorting switch) in operative communication with the control module 400 that, when activated, causes the material to follow an alternative route. For instance, the outfeed conveyor belt 502b can comprise segments of conveyor belts 502, at least one of which is pivotally attached so as to allow it to swing like a flap. When all the segments are in alignment (e.g., the flapping segment is not actuated), the material flows over the segments in a contiguous manner. When the flapping segment is actuated, it rotates (e.g. downward) to allow material to be directed downward and fall through to another outfeed conveyor belt 502b that is located underneath the segmented outfeed conveyor belt 502b. When the inspection system 100 detects a foreign object, the computer device 108 can track the position of the suspected foreign object based on the timestamp, the grid coordinates, and the speed of the conveyance system. Either at a user's discretion (e.g., via the user interface) or automatically by the computer device 108, the control module 400 can be used to control the separator unit 600 and cause the portion of the material suspected to have the foreign object to be removed from the material stream to allow for removal of the foreign object. Once the foreign object has been removed, the formally rejected material can be re-inserted it in to a material flow path for inspection by a different inspection technique (e.g., MD, NIR, XR, human inspection, etc.) and/or the inventive inspection technique.

Embodiments can relate to a method for inspection. The method can involve positioning a background 102 adjacent an inspection zone, the background having a background property defined by a background emission, a background absorbance, and a background reflectance.

The method can involve directing material of a material flow into the inspection zone 104, the material having a material property defined by a material emission, a material absorbance, and a material reflectance.

The method can involve detecting whether the material property differs from the background property by at least deducting EMR of the background from EMR of the material.

In some embodiments, the method can involve directing EMR into the inspection zone 104 so that the EMR will interact with the background 102 and will interact with the material when the material travels into the inspection zone 104.

In some embodiments, the method can involve segmenting the inspection zone 104 by a longitudinal plane into a first inspection zone side 104a and a second inspection zone side 104b. The method can further involve positioning a first background 102a in the first inspection zone side 104a and a second background 102b in the second inspection zone side 104b.

In some embodiments, the method can involve directing EMR into the inspection zone 104 so that EMR will interact with the first background 102a, the second background 102b, and the material when the material travels into the inspection zone.

In some embodiments, the method can involve displaying an image or graphical representation of the material property and the background property.

In some embodiments, the method can involve separating and removing material from the material flow when the material property differs from the background property.

It will be understood that modifications to the embodiments disclosed herein can be made to meet a particular set of design criteria. For instance, any other component or process step can be any suitable number or type of each to meet a particular objective. Therefore, while certain exemplary embodiments of the system and method of using and making the same have been discussed and illustrated, it is to be distinctly understood that the invention is not limited thereto but can be otherwise variously embodied and practiced within the scope of the following claims.

It will be appreciated that some components, features, and/or configurations can be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein. Additionally, the disclosure of a range of values is a disclosure of every numerical value within that range, including the end points.

What is claimed is:

1. An inspection system, comprising:
a background positioned adjacent an inspection zone, the inspection zone being configured and arranged to receive material for transport into the inspection zone;
an illumination source configured to generate and direct electromagnetic radiation (EMR) into the inspection zone so that the EMR will interact with the background and will interact with the material when the material travels into the inspection zone; and
an image capturing device configured to receive background EMR from the background and material EMR from the material that will travel into the inspection zone;
wherein the background has a background property defined by a background emission, a background absorbance, and a background reflectance, the background property being matched in EMR to a material EMR of material to be transported into the inspection zone, the material having a material property defined by a material emission, a material absorbance, and a material reflectance; and
wherein the image capturing device includes a processor configured to detect a foreign object within material when transported into the inspection zone by deducting the background EMR from the material EMR.

2. The inspection system recited in claim 1, in combination with the material positioned in the inspection zone.

3. The inspection system recited in claim 2, in combination with the foreign object within the material positioned in the inspection zone.

4. The inspection system recited in claim 1, wherein:
the material is meat.

5. The inspection system recited in claim 1, comprising:
a computer device in operative communication with the image capturing device, the computer device having a display for displaying an image or graphical representation of the material property and the background property.

6. The inspection system recited in claim 1, wherein:
the material includes: a first material having a first material property; and a foreign object material having a second material property;
the first material property equals the background property; and
the second material property does not equal the background property.

7. The inspection system recited in claim 6, wherein:
the illumination source is configured to generate EMR having a wavelength in the visible spectrum;
the image capturing device is an optical camera; and
the first material property causes the EMR interacted therewith to be within the red color spectrum and the background property causes the EMR interacted therewith to be within the red color spectrum.

8. The inspection system recited in claim 1, wherein:
the inspection zone is segmented by a longitudinal plane into a first inspection zone side and a second inspection zone side;
the background includes a first background located in the first inspection zone side and a second background located in the second inspection zone side;
the material will travel into the inspection zone between the first background and the second background; and
the illumination source is configured to direct the EMR into the inspection zone so that the EMR will interact with the first background, the second background, and the material when the material travels into the inspection zone.

9. The inspection system recited in claim 8, wherein:
the image capturing device includes a first image capturing device and a second image capturing device;
the first image capturing device is configured to detect whether the material property differs from the background property of the first background; and
the second image capturing device is configured to detect whether the material property differs from the background property of the second background.

10. A material processing system, comprising:
a conveyor system having a conveyor belt configured to carry material, the conveyor belt including an outfeed conveyor belt being positioned so that the material will fall through an inspection zone and land on the outfeed conveyor belt; and
an inspection system having:
a background positioned adjacent the inspection zone, the inspection zone being configured and arranged to receive the material for transport into the inspection zone;
an illumination source configured to generate and direct electromagnetic radiation (EMR) into the inspection zone so that the EMR will interact with the background and will interact with the material when the material travels into the inspection zone; and
an image capturing device configured to receive background EMR from the background and from the material that will travel into the inspection zone;
wherein:
the background has a background property defined by a background emission, a background absorbance, and a background reflectance, the background property being matched in EMR to a material EMR of a material to be transported into the inspection zone, the material having a material property defined by a material emission, a material absorbance, and a material reflectance; and
the image capturing device includes a processor configured to detect a foreign object within material when transported into the inspection zone by deducting the background EMR from the material EMR.

11. The material processing recited in claim 10, wherein:
the material is meat and the foreign object is a contaminant.

12. The material processing recited in claim 10, comprising:
a computer device in operative communication with the image capturing device, the computer device having a display for displaying an image or graphical representation of the background property and the material property;

wherein the computer device includes a control module to control the operation of the conveyor belt.

13. The material processing recited in claim 10, comprising:

a separator unit configured to separate and remove the foreign object from the conveyor belt.

14. A method for inspection, the method comprising:

positioning a background adjacent an inspection zone, the background having a background property defined by a background emission, a background absorbance, and a background reflectance;

directing material of a material flow into the inspection zone, the material having a material property defined by a material emission, a material absorbance, and a material reflectance; and detecting whether the material property differs from the background property by at least deducting electromagnetic radiation (EMR) of the background from EMR of the material.

15. The method recited in claim 14, comprising:

directing EMR into the inspection zone so that the EMR will interact with the background and will interact with the material when the material travels into the inspection zone.

16. The method recited in claim 14, comprising:

segmenting the inspection zone by a longitudinal plane into a first inspection zone side and a second inspection zone side; and positioning a first background in the first inspection zone side and a second background in the second inspection zone side.

17. The method recited in claim 16, comprising:

directing EMR into the inspection zone so that EMR will interact with the first background, the second background, and the material when the material travels into the inspection zone.

18. The method recited in claim 14, comprising:

displaying an image or graphical representation of the material property and the background property.

19. The method recited in claim 14, comprising:

separating and removing material from the material flow when the material property differs from the background property.

* * * * *